United States Patent [19]

Lauster

[11] 4,066,566

[45] Jan. 3, 1978

[54] DENTURE CLEANER

[75] Inventor: Frederick L. Lauster, Massillon, Ohio

[73] Assignee: Lafant Research Company, Canton, Ohio

[21] Appl. No.: 672,390

[22] Filed: Mar. 31, 1976

[51] Int. Cl.$^2$ ................................................. C11D 7/36
[52] U.S. Cl. .................................... 252/136; 252/135; 252/142; 252/145; 252/106; 134/42
[58] Field of Search ............... 252/135, 136, 142, 145, 252/106; 134/42

[56] References Cited

U.S. PATENT DOCUMENTS

| | | | |
|---|---|---|---|
| 3,223,643 | 12/1965 | Law | 252/106 |
| 3,785,986 | 1/1974 | Lauster | 252/136 |
| 3,812,046 | 5/1974 | Lancy | 252/106 |
| 3,855,140 | 12/1974 | Billany et al. | 252/106 |
| 3,899,437 | 8/1975 | Regan et al. | 252/106 |
| 3,960,745 | 1/1976 | Billany et al. | 252/106 |

*Primary Examiner*—Mayer Weinblatt
*Attorney, Agent, or Firm*—Isler and Ornstein

[57] ABSTRACT

A denture cleaner is provided which is non-abrasive and is highly effective for quickly and easily removing stains and tartar deposits from dentures embodying plastic or porcelain teeth and other materials used in dentures. The cleaner is effective for cleaning both full and removable partial dentures, as well as for polishing gold or chromium alloy clasps and removable orthodontic and other oral dental appliances, and has high stability under conditions involving both high and low temperatures. It is characterized by the inclusion therein of Hyamine 3500 and Pluronic P65, which are completely compatible with the other ingredients of the denture cleaner.

2 Claims, No Drawings

DENTURE CLEANER

This invention relates generally to denture cleaners.

In my U.S. Pat. No. 3,785,986, a denture cleaner is described, which contains, among other ingredients, a small amount of a biostat sold by Onyx Chemical Company, of Jersey City, N.Y., under the trademark "BTC 2125M, 50% active," and consisting of the following ingredients, in the percentage proportions by weight indicated.

| Active ingredients | Percent |
|---|---|
| n-Alkyl (60% $C_{14}$, 30% $C_{16}$, 5% $C_{12}$, 5% $C_{18}$) dimethyl benzyl ammonium chlorides | 25 |
| n-Alkyl (68% $C_{12}$, 32% $C_{14}$) dimethyl ethylbenzyl chlorides | 25 |
| Water | 50 |
| | 100 | and a substantial amount of a biodegradable liquid, anhydrous water-soluble nonionic detergent and surfactant, sold by Rohm and Haas Company, of Philadelphia, Pa., under the trademark Triton X-102, and consisting of octyl phenoxy polyethoxy ethanol containing 12–13 moles of ethylene oxide.

The aforesaid denture cleaner also contained small amounts of a blue dye and a perfume or flavoring agent.

In the use of the aforesaid denture cleaner, it has been found that BTC 2125M is not compatible with the remainder of the cleaner, and has a tendency to cause a breakdown of the mixture.

Moreover, the Triton X-102 was also found to be incompatible with the remainder of the cleaner, and also to have a tendency to cause a breakdown of the mixture, in addition to the fact that it has a negative bitterness or taste and a high toxicity.

The dye and flavoring agent are also incompatible and cause a breakdown of the mixture, and have been found to be unnecessary.

I have found that the aforesaid denture cleaner can be substantially improved by substituting for the BTC 2125M a very small amount of Hyamine 3500, substituting for the Triton X-102 substantially the same amount of Pluronic 65, and omitting the dye and flavoring agent.

Hyamine 3500 is a trademark of Rohm and Haas Company, for a selected blend of alkyl dimethyl benzyl ammonium chlorides, having exceptional microbicidal effectiveness in hard water, and is available in two forms, that is, as a 50% aqueous solution, and an 80% concentrate in ethanol. It is an effective bactericide useful as a disinfectant, sanitizer, and deodorant in liquid and powdered formulations where high germicidal activity in hard water is required.

Hyamine 3500 is defined in the Concise Chemical and Technical Dictionary, Edited by H. Bennett, and published in 1974, as n-alkyl (40% $C_{12}$, 50% $C_{14}$, 10% $C_{16}$) dimethyl benzyl ammonium chloride.

Pluronics is a trademark of Wyandotte Chemicals Corp. for a series of nonionic surface-active agents prepared by the addition of ethylene oxide to polypropylene glycols, available in liquid paste, flake and powder form, and all 100% active agent. In the Concise Chemical and Technical Dictionary, Edited by H. Bennett, and published in 1974, "Pluronic" is defined as polyoxypropylene with polyoxyethylene group at either end. Pluronic has also been described as a family name for an almost unlimited number of 100% active, nonionic surfactant polyols. They are available from BASF Wyandotte Corp., of Wyandotte, Mich.

In the denture cleaner of the present invention, the Pluronic known as Pluronic P65 is used, having an average molecular weight of 3400, a specific gravity of 1.06, and a melting point of 30° C., since this particular Pluronic is available in paste form, is tasteless and odorless, and non-toxic, and completely compatible with the remainder of the denture cleaner. Pluronic (P65) is also described or defined on page 167 of "McCutcheon's, Detergents are Emulsifiers" (1969) as condensate of ethylene oxide with hydropholic basis formed by condensing propylene oxide with propylene glycol.

The improved denture cleaner, to be presently described, is non-abrasive, and highly effective to quickly and easily remove stains and tartar deposits from dentures embodying plastic or porcelain teeth and other denture materials.

It is effective to clean both full and removable partial dentures, as well as to polish gold or chromium alloy clasps and removable orthodontic oral or dental appliances.

Moreover, it has great stability under conditions involving both high and low temperatures.

Other objects and advantages of the invention will become apparent during the course of the following description of the denture cleaner.

The denture cleaner, in accordance with the invention, consists of the following ingredients, in the percentage proportions by weight indicated:

| | Percentage by weight | |
|---|---|---|
| | Range | Preferred |
| Water | 20–24 | 23.04 |
| Sodium phosphate, dibasic | 3.6–4.4 | 4.00 |
| Phosphoric acid (85%) | 22.00–26.80 | 24.41 |
| Glycerin | .9–1.1 | 1.00 |
| Stannic oxide | .45–.55 | .50 |
| Hyamine 3500 | .03–.07 | .05 |
| Pluronic P65 | 42.3–51.7 | 47.00 |
| | 100 | 100 |

Sodium phosphate, dibasic, also known as DSP; disodium phosphate; hydrosodium phosphate, and disodium orthophosphate, (a) $Na_2HPO_4$; (b) $Na_2HPO_4.2H_2O$; (c) $Na_2HPO_4.7H_2O$; (d) $Na_2HPO_4.12H_2O$, is available in the form of translucent crystals or white powder, soluble in water. The crystal or granular form is used in this formulation. Its function or use in this denture cleaner is to buffer the phosphoric acid and to help neutralize any possible caustic effect of the acid.

Phosphoric acid ($H_3PO_4$), is also known as orthophosphoric acid, and is a clear, colorless, sparkling liquid or a transparent crystalline solid, depending on the concentration and temperature. At ordinary atmospheric temperature (20° C.), the 50% and 75% strengths are mobile liquids, the 85% strength is of a syrupy consistency, while the 100% acid is in the form of crystals, soluble in water. An 85% strength is preferred, because it is of a technical grade, and is more readily available and safer to work with for commercial production. Its function in the present denture cleaner is to provide the necessary acid properties for proper denture cleaning.

Glycerin, also known as glycerol, and glycyl alcohol $C_3H_5(OH)_3$, is a clear, colorless, or pale yellow, odorless, syrupy liquid, having a sweet, warm taste, and soluble in water. Its function or use in the present denture cleaner is to help protect the tissue from burns.

Stannic oxide, also known as stannic anhydride; tin peroxide; stannic acid; flowers of tin, tin ash, and tin anhydride $SnO_2$, or $SnO_2.nH_2O$, is a white powder, anhydrous or containing variable amounts of water. It is insoluble in water. One of its uses is as a polishing powder for steel; hence its adaptability, in the present denture cleaner, as a polishing material for dentures embodying metallic parts.

Hyamine 3500 and Pluronic P65 have been defined and described above, so that no further description thereof is believed to be necessary.

It may be noted, however, that the Hyamine 3500 and the Pluronic P65 form a completely stable mixture with the other ingredients, are completely compatible with each other and the other ingredients of the mixture, and are tasteless and odorless, as well as non-toxic.

The aforesaid denture cleaner is preferably prepared in the following manner:

(1) A vessel is filled with the proportion of water indicated.
(2) The sodium phosphate, dibasic, is added to the water with good agitation.
(3) The phosphoric acid is added very slowly, with slow mixing or gentle agitation.
(4) The glycerin, stannic oxide, Hyamine 3500, and Pluronic P65 are separately mixed together, and this mixture is heated to a temperature of about 125°–150° F., after which it is added to the mixture of (1), (2) and (3) above.

The denture cleaner, as thus prepared, is preferably packaged in plastic containers.

The cleaner is normally used by applying it to the denture, and brushing it over the denture with a water-dampened brush, for 30 seconds or more, after which the denture is thoroughly rinsed with water.

For removal of heavy tartar and stains accumulated over years, the cleaner, in an amount about the size of a quarter, is placed on the dry denture, and rubbed over the areas desired, after which the denture is immersed in an amount of warm water sufficient to just cover the denture. After about 15 minutes, the denture is further cleaned by use of the normal procedure described in the preceding paragraph. This entire procedure is then repeated until tartar and stain are removed, after which a normal 30 second cleaning may be used.

The denture cleaner may also be packaged in an aerosol container, which contains a compatible aerosol propellant, enabling the cleaner to be sprayed onto the denture, and then brushed onto the denture, after which the denture is rinsed with water.

Another method of using the denture cleaner is to mix the ingredients, minus the water, with a suitable organic binder, and then compress the mixture into the form of a tablet or wafer, which can be dropped into a glass of water, the denture placed in the glass, and permitted to remain in the glass overnight.

It is thus seen that I have provided a denture cleaner which is non-abrasive, and is highly effective for quickly and easily removing stains and tartar deposits from dentures embodying plastic or porcelain teeth, and other materials conventionally used in making dentures.

It is also seen that I have provided a denture cleaner which is effective to clean both full and removable partial dentures, as well as to polish gold or chromium alloy clasps and removable orthodontic oral or dental appliances.

It is further seen that I have provided a denture cleaner of great stability, under conditions involving both high and low temperatures, and which is characterized by the inclusion therein of Hyamine 3500 and Pluronic P65, which form a completely stable mixture with the other ingredients of the mixture, which are completely compatible with each other and the other ingredients of the mixture, and are tasteless, and odorless, as well as non-toxic.

It is understood that slight changes may be made in the formula or composition of the denture cleaner as described, without departing from the spirit of the invention or the scope of the appended claims.

I claim:

1. A method of removing tarter and stain from a denture with a cleaner, in parts by weight, consisting of from 20 to 24% of water, from 3.6 to 4.4% of dibasic sodium phosphate, from 22 to 26.80% of 85% strength phosphoric acid, from 0.9 to 1.1% of glycerin, from 0.45 to 0.55% of stannic oxide, from 0.03 to 0.07% of n-alkyl (50% $C_{14}$, 40% $C_{12}$, 10% $C_{16}$) dimethyl benzyl ammonium chloride, and from 42.3 to 51.7% of condensate of ethylene oxide with hydrophobic base formed by condensing propylene oxide with propylene glycol, and having an average molecular weight of 3400, comprising applying said composition to a dry denture, immersing said denture in warm water for about 15 minutes and rinsing the denture in water.

2. A method of removing tarter and stain from a denture with a cleaner, in parts by weight, consisting of about 23.04% of water, about 4% of dibasic sodium phosphate, about 24.41% of 85% strength phosphoric acid, about 1% of glycerin, about 0.50% of stannic oxide, about 0.05% of n-alkyl (50% $C_{14}$, 40% $C_{12}$, 10% $C_{16}$) dimethyl benzyl ammonium chloride and about 47% of condensate of ethylene oxide with hydrophobic base formed by condensing propylene oxide with propylene glycol and having an average molecular weight of 3400, comprising applying said cleaner to a dry denture, immersing said denture in warm water for about 15 minutes and rinsing the denture in water.

* * * * *